(12) United States Patent
Kamath et al.

(10) Patent No.: US 7,302,294 B2
(45) Date of Patent: Nov. 27, 2007

(54) SUBCUTANEOUS CARDIAC SENSING AND STIMULATION SYSTEM EMPLOYING BLOOD SENSOR

(75) Inventors: Apurv Kamath, Solana Beach, CA (US); Paul Haefner, Circle Pines, MN (US); Darrell Orvin Wagner, Isanti, MN (US); Marina Brockway, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 302 days.

(21) Appl. No.: 10/817,749

(22) Filed: Apr. 2, 2004

(65) Prior Publication Data
US 2004/0220629 A1 Nov. 4, 2004

Related U.S. Application Data

(60) Provisional application No. 60/462,272, filed on Apr. 11, 2003.

(51) Int. Cl.
*A61N 1/365* (2006.01)
(52) U.S. Cl. .......................................................... 607/6
(58) Field of Classification Search ................... 607/6, 607/14, 18, 22; 600/6
See application file for complete search history.

(56) References Cited

U.S. PATENT DOCUMENTS

| | | |
|---|---|---|
| 4,562,841 A | 1/1986 | Brockway et al. |
| 4,784,162 A | 11/1988 | Ricks et al. |
| 4,827,943 A | 5/1989 | Bornn et al. |
| 4,953,551 A | 9/1990 | Mehra et al. |
| 5,036,849 A | 8/1991 | Hauck et al. |
| 5,133,353 A | 7/1992 | Hauser |

(Continued)

FOREIGN PATENT DOCUMENTS

EP 0 488 512 A 3/1992

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—George Manuel
*Assistant Examiner*—Christopher A. Flory
(74) *Attorney, Agent, or Firm*—Hollingsworth & Funk, LLC

(57) ABSTRACT

Cardiac systems and methods using ECG and blood information for arrhythmia detection and discrimination. Detection circuitry is configured to produce an ECG. An implantable blood sensor configured to produce a blood sensor signal is coupled to a processor. The processor is coupled to the detection and energy delivery circuitry, and used to evaluate and treat cardiac rhythms using both the cardiac electrophysiologic and blood sensor signals. The blood sensor is configured for subcutaneous non-intrathoracic placement and provided in or on the housing, on a lead coupled to the housing, and/or separate to the housing and coupled to the processor via hardwire or wireless link. The blood sensor may be configured for optical sensing, using a blood oxygen saturation sensor or pulse oximeter. A cardiac rhythm may be evaluated using the electrocardiogram signal and the blood sensor signal, and tachyarrhythmias may be treated after confirmation using the blood sense signal.

52 Claims, 11 Drawing Sheets

U.S. PATENT DOCUMENTS

| | | |
|---|---|---|
| 5,170,784 A | 12/1992 | Ramon et al. |
| 5,176,137 A * | 1/1993 | Erickson et al. ............... 607/4 |
| 5,179,945 A | 1/1993 | Van Hofwegen et al. |
| 5,203,348 A | 4/1993 | Dahl et al. |
| 5,209,229 A | 5/1993 | Gilli |
| 5,230,337 A | 7/1993 | Dahl et al. |
| 5,261,400 A | 11/1993 | Bardy |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,330,505 A * | 7/1994 | Cohen ........................ 607/6 |
| 5,331,966 A | 7/1994 | Bennett et al. |
| 5,342,404 A | 8/1994 | Alt et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,417,714 A | 5/1995 | Levine et al. |
| 5,439,482 A | 8/1995 | Adams et al. |
| 5,441,518 A | 8/1995 | Adams et al. |
| 5,464,434 A * | 11/1995 | Alt ............................ 607/6 |
| 5,468,254 A | 11/1995 | Hahn et al. |
| 5,531,779 A | 7/1996 | Dahl et al. |
| 5,540,727 A | 7/1996 | Tockman et al. |
| 5,545,186 A | 8/1996 | Olson et al. |
| 5,545,202 A | 8/1996 | Dahl et al. |
| 5,556,421 A | 9/1996 | Prutchi et al. |
| 5,601,611 A * | 2/1997 | Fayram et al. ................ 607/6 |
| 5,603,732 A | 2/1997 | Dahl et al. |
| 5,606,969 A | 3/1997 | Butler et al. |
| 5,620,466 A | 4/1997 | Haefner et al. |
| 5,634,938 A | 6/1997 | Swanson et al. |
| 5,641,326 A | 6/1997 | Adams |
| 5,662,688 A | 9/1997 | Haefner et al. |
| 5,697,953 A | 12/1997 | Kroll et al. |
| 5,704,365 A | 1/1998 | Albrecht et al. |
| 5,724,984 A | 3/1998 | Arnold et al. |
| 5,827,326 A | 10/1998 | Kroll et al. |
| 5,836,987 A | 11/1998 | Baumann et al. |
| 5,855,593 A | 1/1999 | Olson et al. |
| 5,895,414 A | 4/1999 | Sanchez-Zambrano |
| 5,916,243 A | 6/1999 | KenKnight et al. |
| 5,919,141 A | 7/1999 | Money et al. |
| 5,957,956 A | 9/1999 | Kroll et al. |
| 5,961,446 A | 10/1999 | Beller et al. |
| 5,961,450 A | 10/1999 | Merchant et al. |
| 6,044,298 A | 3/2000 | Salo et al. |
| 6,050,940 A | 4/2000 | Braun et al. |
| 6,055,454 A | 4/2000 | Heemels |
| 6,122,536 A | 9/2000 | Sun et al. |
| 6,141,581 A | 10/2000 | Olson et al. |
| 6,144,879 A | 11/2000 | Gray |
| 6,148,230 A | 11/2000 | KenKnight |
| 6,198,952 B1 | 3/2001 | Miesel |
| 6,221,011 B1 | 4/2001 | Bardy |
| 6,259,947 B1 | 7/2001 | Olson et al. |
| 6,270,457 B1 | 8/2001 | Bardy |
| 6,277,072 B1 | 8/2001 | Bardy |
| 6,280,380 B1 | 8/2001 | Bardy |
| 6,280,462 B1 | 8/2001 | Hauser et al. |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,375,614 B1 | 4/2002 | Braun et al. |
| 6,398,728 B1 | 6/2002 | Bardy |
| 6,409,675 B1 | 6/2002 | Turcott |
| 6,415,174 B1 | 7/2002 | Bebehani et al. |
| 6,438,410 B2 | 8/2002 | Hsu et al. |
| 6,440,066 B1 | 8/2002 | Bardy |
| 6,454,708 B1 | 9/2002 | Ferguson et al. |
| 6,480,733 B1 | 11/2002 | Turcott |
| 6,487,443 B2 | 11/2002 | Olson et al. |
| 6,491,639 B1 | 12/2002 | Turcott |
| 6,512,940 B1 | 1/2003 | Brabec et al. |
| 6,522,915 B1 | 2/2003 | Ceballos et al. |
| 6,564,106 B2 | 5/2003 | Guck et al. |
| 6,607,509 B2 | 8/2003 | Bobroff et al. |
| 6,615,083 B2 | 9/2003 | Kupper |
| 6,622,046 B2 | 9/2003 | Fraley et al. |
| 6,628,986 B1 | 9/2003 | Mouchawar et al. |
| 6,786,917 B1 * | 9/2004 | Schiller et al. ............. 600/465 |
| 6,976,963 B2 * | 12/2005 | Clift .......................... 600/484 |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107552 A1 | 8/2002 | Krig et al. |
| 2002/0107559 A1 | 8/2002 | Sanders et al. |
| 2002/0120299 A1 | 8/2002 | Ostroff et al. |
| 2002/0147474 A1 | 10/2002 | Seim et al. |
| 2003/0004546 A1 | 1/2003 | Casey |
| 2003/0004552 A1 | 1/2003 | Plombon et al. |
| 2003/0023175 A1 | 1/2003 | Arzbaecher et al. |
| 2003/0036778 A1 | 2/2003 | Ostroff et al. |
| 2003/0045904 A1 | 3/2003 | Bardy et al. |
| 2003/0069609 A1 | 4/2003 | Thompson |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0212436 A1 | 11/2003 | Brown |
| 2004/0172066 A1 | 9/2004 | Wagner et al. |
| 2004/0220633 A1 | 11/2004 | Wagner et al. |
| 2004/0230129 A1 | 11/2004 | Haefner |
| 2004/0230230 A1 | 11/2004 | Lindstrom et al. |

| | | |
|---|---|---|
| 2005/0119708 A1 | 6/2005 | Haefner |

FOREIGN PATENT DOCUMENTS

| WO | WO 92/20402 | 11/1992 |
|---|---|---|
| WO | WO 03/020367 A | 3/2003 |

OTHER PUBLICATIONS

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*, Europace Supplements, vol. 2, Jun. 2001 at column 778, p. B83.

Stirbis et al., *Optimizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in a Eight-Month-Old Infant with Ventricular Fibrillation Arising from a Myocardial Fibroma*, PACE, vol 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

\* cited by examiner

SUBCUTANEOUS CARDIAC SENSING AND STIMULATION SYSTEM EMPLOYING BLOOD SENSOR

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to implantable cardiac monitoring and stimulation devices and, more particularly, to cardiac systems and methods using subcutaneously sensed blood information.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical Implantable cardioverter/defibrillators (ICDs) include one or more endocardial leads to which at least one defibrillation electrode is connected. Such ICDs are capable of delivering high-energy shocks to the heart, interrupting the ventricular tachyarrhythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. Primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure.

SUMMARY OF THE INVENTION

The present invention is directed to cardiac monitoring and/or stimulation methods and systems that, in general, provide transthoracic monitoring, defibrillation therapies, pacing therapies, or a combination of these capabilities. Embodiments of the present invention include those directed to subcutaneous cardiac monitoring and/or stimulation methods and systems that evaluate a cardiac rhythm and/or treat a cardiac arrhythmia using both ECG and blood information.

According to one embodiment of the invention, a medical device includes a housing configured for subcutaneous non-intrathoracic placement. Detection circuitry is provided in the housing and configured to produce a cardiac electrophysiologic signal. Energy delivery circuitry is also provided in the housing. At least one electrode configured for subcutaneous non-intrathoracic placement is coupled to the detection and energy delivery circuitry. An implantable blood sensor configured to produce a blood sensor signal is also provided with the device, and coupled to a processor provided in the housing. The processor is also coupled to the detection and energy delivery circuitry, and used to evaluate a cardiac rhythm using the cardiac electrophysiologic signal and the blood sensor signal. In one approach, the processor is configured to use a blood sensor signal to verify that the cardiac electrophysiologic signal comprises a cardiac signal, and configured to evaluate a cardiac rhythm using the blood sensor signal and the cardiac electrophysiologic signal comprising the cardiac signal.

The blood sensor may be configured for subcutaneous non-intrathoracic placement and provided in or on the housing, on a lead coupled to the housing, and/or separate from the housing and coupled to the processor via hardwire or wireless link. The blood sensor may include a sensor configured for optical signal sensing, such as a blood oxygen saturation sensor or a pulse oximeter. A suitable pulse oximeter may include two light-emitting diodes and one photodetector. The photodetector may include circuitry having a detection threshold that is periodically adjusted to account for signal variations.

In another configuration, a suitable pulse oximeter may include a first light-emitting diode having a peak light-emission wavelength within a range of about 550 nm and about 750 nm, and a second light-emitting diode having a peak light-emission wavelength within a range of about 750 nm and about 1050 nm. A photoplethysmography circuit may be included as a blood sensor and coupled to the processor. The processor may identify a cardiac rhythm as a tachyarrhythmia using the cardiac electrophysiologic signal and the blood sensor signal.

The processor may identify the cardiac rhythm as a tachyarrhythmia using the cardiac electrophysiologic signal and a relative change in the blood sensor signal, and may also selectively activate and deactivate the blood sensor in response to detecting a tachyarrhythmia. The processor may use the cardiac electrophysiologic signal to activate the blood sensor and evaluate the tachyarrhythmia using the cardiac electrophysiologic signal and the blood sensor signal. The processor may further confirm or refute the presence of the tachyarrhythmia using the cardiac electrophysiologic signal and the blood sensor signal.

The device may deliver a therapy to treat a tachyarrhythmia, and the processor may deactivate the blood sensor before or after delivery of the therapy. The processor may determine a hemodynamic state using the cardiac electrophysiologic signal and the blood sensor signal. In response to detecting an unidentifiable cardiac rhythm using the cardiac electrophysiologic signal, the processor may activate the blood sensor to facilitate identification of the unidentifiable cardiac rhythm using the blood sensor signal. The processor may use the blood sensor signal to assess cardiac function, assess oxygen saturation and changes in oxygen saturation, and/or assess afterload by, for example, analyzing the morphology of the blood sensor signal.

Embodiments of rhythm evaluation methods in accordance with the present invention may involve sensing an electrocardiogram signal at a subcutaneous non-intrathoracic location and acquiring a blood sense signal from a subcutaneous non-intrathoracic sensing location. A cardiac rhythm may be evaluated using the electrocardiogram signal and the blood sensor signal. One approach involves verifying that the electrocardiogram signal comprises a cardiac signal, and evaluating a cardiac rhythm using the blood sense signal and the electrocardiogram signal comprising the cardiac signal. A tachyarrhythmia may be detected using one or both of the electrocardiogram signal and the blood sense signal, such as by performing a rate based analysis or by performing a morphology based analysis.

An activation pattern of the electrocardiogram signal may be analyzed using a plurality of electrodes, and detected tachyarrhythmias may be treated after confirming presence of the tachyarrhythmia using the blood sense signal. The tachyarrhythmia may be discerned from noise using the blood sense signal. Evaluating the cardiac rhythm may also involve detecting a cardiac arrhythmia by performing a correlation (or computing a transfer function) between the electrocardiogram signal and the blood sense signal. Acquiring the blood sense signal may involve selectively powering-up and powering-down a blood sensor that produces the blood sense signal.

Evaluating a cardiac rhythm may involve detecting a tachyarrhythmia using the electrocardiogram signal, powering-up a blood sensor that produces the blood sense signal, confirming presence of the tachyarrhythmia using the blood sense signal, and then powering-down the blood sensor. The blood sense signal may include, for example, blood perfusion information, blood oxygen saturation information, photoplethysmographic information, pulse oximetry information, and/or other information from a blood sensor.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
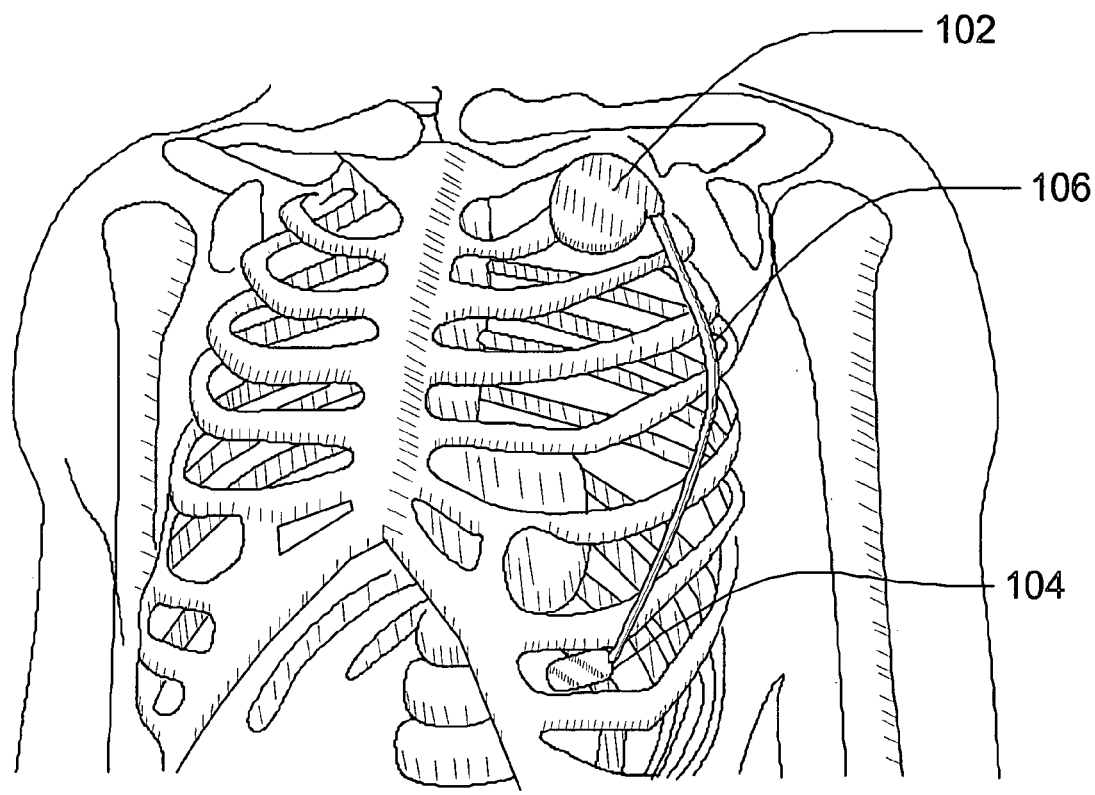
FIGS. 1A and 1B are views of a transthoracic cardiac sensing and/or stimulation device as implanted in a patient in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which is shown by way of illustration, various embodiments in which the invention may be practiced. It is to be understood that other embodiments may be utilized, and structural and functional changes may be made without departing from the scope of the present invention.

System and methods of the present invention may include one or more of the features, structures, methods, or combinations thereof described hereinbelow. For example, implantable cardiac systems and methods in accordance with the present invention may be implemented to include one or more of the advantageous features and/or processes described below. It is intended that such devices and methods need not include all of the features described herein, but may be implemented to include selected features that provide for unique structures and/or functionality. Such devices and methods may be implemented to provide a variety of therapeutic and/or diagnostic functions.

Embodiments of the present invention are directed to implantable cardiac devices (ICDs) having incorporated blood sensor capabilities. Embodiments of the present invention are also directed to systems and methods for discriminating between arrhythmia and normal sinus rhythm (NSR) using blood sensor information. One such implantable device, termed an implantable transthoracic cardiac sensing and/or stimulation (ITCS) device, is described herein to include various advantageous features and/or processes. It is understood that the description of features and processes within the context of an ITCS device is provided for non-limiting illustrative purposes only. For example, various features and processes described herein may be implemented for devices such as cardiac monitors, diagnostic devices, pacemakers, cardioverters/defibrillators, resynchronizers, and the like, including those devices disclosed in the various patents incorporated herein by reference.

In general terms, the ITCS device may be implanted under the skin in the chest region of a patient. The ITCS device may, for example, be implanted subcutaneously such that all or selected elements of the device are located on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively located at different regions near, around, in, or on the heart. Examples of electrode configurations, elements of which may be located in accordance with the present invention, are disclosed in commonly owned, U.S. patent application Ser. No. 10/465,520, filed Jun. 19, 2003, which is hereby incorporated herein by reference in its entirety.

In one configuration, the primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature. In another implementation, one or more electrodes may be located in direct contact with the heart, great vessel or coronary vasculature, such as via one or more leads. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, elements of which may be incorporated in an ITCS device of a type contemplated herein, are disclosed in commonly owned U.S. Pat. Nos. 5,133,353; 5,179,945; 5,314,459; 5,318,597; 5,620,466; and 5,662,688, which are hereby incorporated herein by reference in their respective entireties.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, elements of which may be incorporated in an ITCS device of a type contemplated herein, are disclosed in commonly owned U.S. Pat. Nos. 4,562,841; 5,284,136; 5,036,849; 5,376,106; 5,540,727; 5,836,987; 6,044,298; and 6,055,454, which are hereby incorporated herein by reference in their respective entireties. It is understood that ITCS device configurations may provide for non-physiologic pacing support in addition to, or to the exclusion of, bradycardia and/or anti-tachycardia pacing therapies.

An ITCS device may implement functionality traditionally provided by cardiac diagnostic devices or cardiac monitors as are known in the art, alternatively or additionally to providing cardioversion/defibrillation therapies. Examples of cardiac monitoring circuitry, structures and functionality, elements of which may be incorporated in an ITCS device of a type contemplated herein, are disclosed in commonly owned U.S. Pat. Nos. 5,313,953; 5,388,578; and 5,411,031, which are hereby incorporated herein by reference in their respective entireties.

An ITCS device may implement various anti-tachyarrhythmia therapies, such as tiered therapies. Subcutaneous, cutaneous, and/or external blood sensors may be employed to acquire information for purposes of enhancing tachyarrhythmia detection and termination. It is understood that configurations, features, and combination of features described in the instant disclosure may be implemented in a wide range of implantable medical devices, and that such embodiments and features are not limited to the particular devices described herein.

An ITCS device may be used to implement various diagnostic functions, which may involve performing rate-based, pattern and rate-based, and/or morphological tachyarrhythmia discrimination analyses. Subcutaneous, cutaneous, and/or external blood sensors may be employed to acquire information for purposes of enhancing tachyarrhythmia detection and termination. It is understood that configurations, features, and combination of features described in the instant disclosure may be implemented in a wide range of implantable medical devices, and that such embodiments and features are not limited to the particular devices described herein.

Figure 1B:
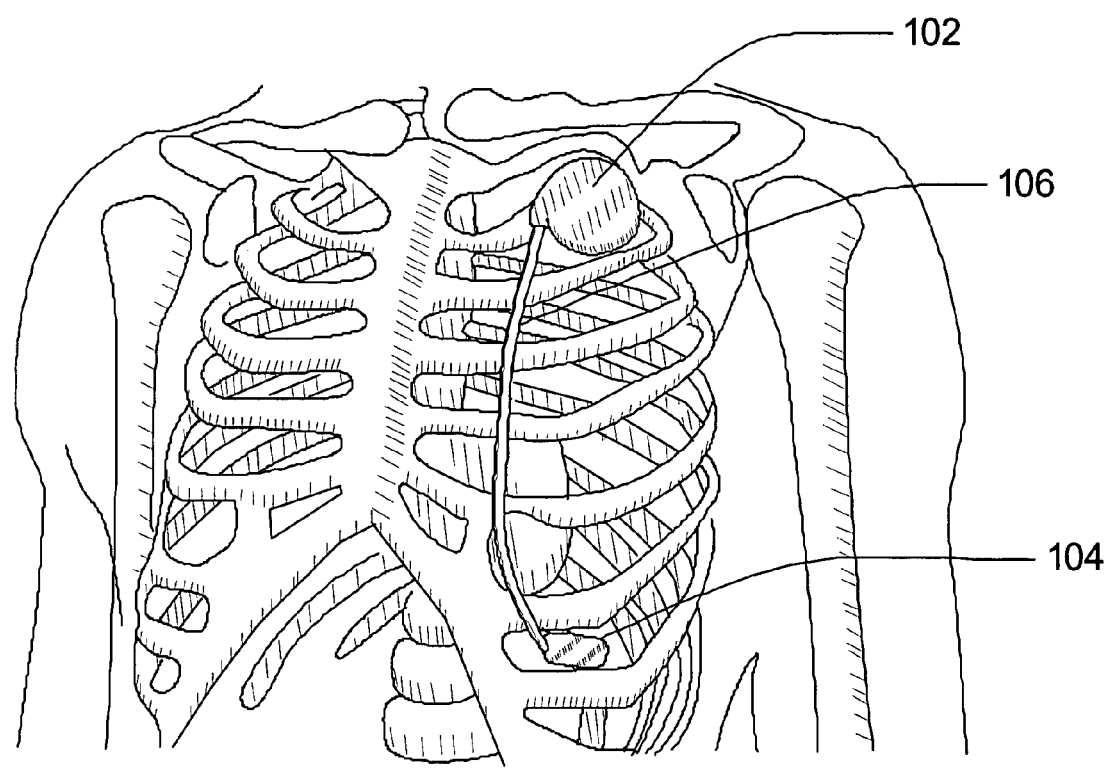

Referring now to FIGS. 1A and 1B of the drawings, there is shown a configuration of an ITCS device implanted in the chest region of a patient at different locations. In the particular configuration shown in FIGS. 1A and 1B, the ITCS device includes a housing 102 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors such as blood sensors used in accordance with embodiments of the present invention. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 1A and 1B, a subcutaneous electrode 104 may be positioned under the skin in the chest region and situated distal from the housing 102. The subcutaneous and, if applicable, housing electrode(s) may be located about the heart at various locations and orientations, such as at various anterior and/or posterior locations relative to the heart. The subcutaneous electrode 104 is electrically coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure may be formed from a structural plastic, composite or metallic material, and includes, or is covered by, a biocompatible material. Appropriate electrical isolation between the housing 102 and subcutaneous electrode 104 is provided in cases where the elongated structure is formed from an electrically conductive material, such as metal.

In one configuration, the rigid electrode support assembly and the housing 102 define a unitary structure (i.e., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly. Alternatively, a mechanical/electrical coupler may be used to establish mechanical and electrical connections between the rigid electrode support assembly and housing 102. In such a configuration, a variety of different electrode support assemblies of varying shapes, sizes, and electrode configurations may be made available for physically and electrically connecting to a standard ITCS device housing 102.

An ITCS device may incorporate circuitry, structures and functionality of the subcutaneous implantable medical devices disclosed in commonly owned U.S. Pat. Nos. 5,203,348; 5,230,337; 5,360,442; 5,366,496; 5,391,200; 5,397,342; 5,545,202; 5,603,732; and 5,916,243, which are hereby incorporated herein by reference in their respective entireties.

Figure 1C:
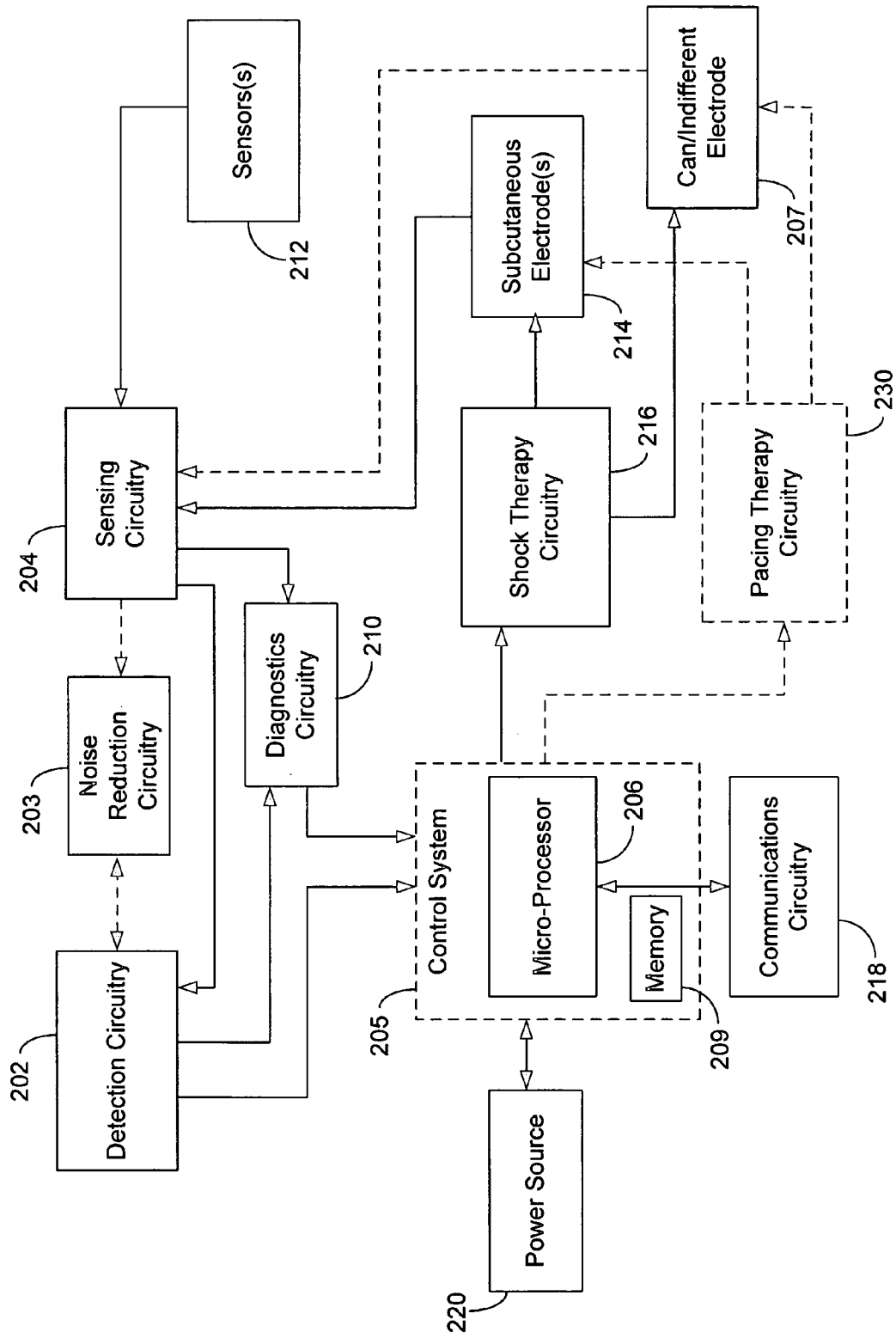
FIG. 1C is a block diagram showing various components of a transthoracic cardiac sensing and/or stimulation device in accordance with an embodiment of the present invention.

FIG. 1C is a block diagram depicting various components of an ITCS device in accordance with one configuration. According to this configuration, the ITCS device incorporates a processor-based control system 205 which includes a micro-processor 206 coupled to appropriate memory (volatile and/or non-volatile) 209, it being understood that any logic-based control architecture may be used. The control system 205 is coupled to circuitry and components to sense, detect, and analyze electrical signals produced by the heart and deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high-energy pulses for cardioversion or defibrillation.

Cardiac signals are sensed using the subcutaneous electrode(s) 214 and the can or indifferent electrode 207 provided on the ITCS device housing. Cardiac signals may also be sensed using only the subcutaneous electrodes 214, such as in a non-active can configuration. As such, unipolar, bipolar, or combined unipolar/bipolar electrode configurations may be employed. The sensed cardiac signals are received by sensing circuitry 204, which includes sense amplification circuitry and may also include filtering circuitry and an analog-to-digital (A/D) converter. The sensed cardiac signals processed by the sensing circuitry 204 may be received by noise reduction circuitry 203, which may further reduce noise for signals used by the detection circuitry 202. Noise reduction circuitry 203 may also be incorporated after detection circuitry 202 in cases where high power or computationally intensive noise reduction algorithms are required.

In the illustrative configuration shown in FIG. 1C, the detection circuitry 202 is coupled to, or otherwise incorporates, noise reduction circuitry 203. The noise reduction circuitry 203 operates to improve the signal-to-noise ratio of sensed cardiac signals by removing noise content of the sensed cardiac signals introduced from various sources. Typical types of transthoracic cardiac signal noise includes electrical noise and noise produced from skeletal muscles, for example.

Detection circuitry 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode. Examples of arrhythmia detection and discrimination circuitry, structures, and techniques, elements of which may be implemented by an ITCS device of a type contemplated herein, are disclosed in commonly owned U.S.

Pat. Nos. 5,301,677 and 6,438,410, which are hereby incorporated herein by reference in their respective entireties.

The detection circuitry 202 communicates cardiac signal information to the control system 205. Memory circuitry 209 of the control system 205 contains parameters for operating in various sensing, defibrillation, and pacing modes, and stores data indicative of cardiac signals received by the detection circuitry 202. The memory circuitry 209 may also be configured to store historical ECG, blood information, and therapy data, which may be used for various purposes and transmitted to an external receiving device as needed or desired.

In certain configurations, the ITCS device may include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the subcutaneous electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Examples of ICD high energy delivery circuitry, structures and functionality, elements of which may be incorporated in an ITCS device of a type contemplated herein, are disclosed in commonly owned U.S. Pat. Nos. 5,372,606; 5,411,525; 5,468,254; and 5,634,938, which are hereby incorporated herein by reference in their respective entireties.

In accordance with another configuration, an ITCS device may incorporate a cardiac pacing capability in addition to cardioversion and/or defibrillation capabilities. As is shown in dotted lines in FIG. 1C, the ITCS device may include pacing therapy circuitry 230, which is coupled to the control system 205 and the subcutaneous and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated. A pacing regimen may be modified by the control system 205.

A number of cardiac pacing therapies are particularly useful in a transthoracic cardiac stimulation device. Such cardiac pacing therapies may be delivered via the pacing therapy circuitry 230 as shown in FIG. 1C. Alternatively, cardiac pacing therapies may be delivered via the shock therapy circuitry 216, which effectively obviates the need for separate pacemaker circuitry.

The ITCS device shown in FIG. 1C may be configured to receive signals from one or more physiologic and/or non-physiologic sensors 212. Depending on the type of sensor employed, signals generated by the sensors may be communicated to transducer circuitry coupled directly to the detection circuitry or indirectly via the sensing circuitry. It is noted that certain sensors may transmit sense data to the control system 205 without processing by the detection circuitry 202.

Communications circuitry 218 is coupled to the microprocessor 206 of the control system 205. The communications circuitry 218 allows the ITCS device to communicate with one or more receiving devices or systems situated external to the ITCS device. By way of example, the ITCS device may communicate with a patient-worn, portable or bedside communication system via the communications circuitry 218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the ITCS device via the communications circuitry 218. It is noted that physiologic or non-physiologic sensors equipped with wireless transmitters or transceivers may communicate with a receiving system external of the patient.

The communications circuitry 218 may allow the ITCS device to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the ITCS device and the programmer unit during and after implant. Using a programmer, a physician is able to set or modify various parameters used by the ITCS device. For example, a physician may set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive RF energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

Figure 1D:
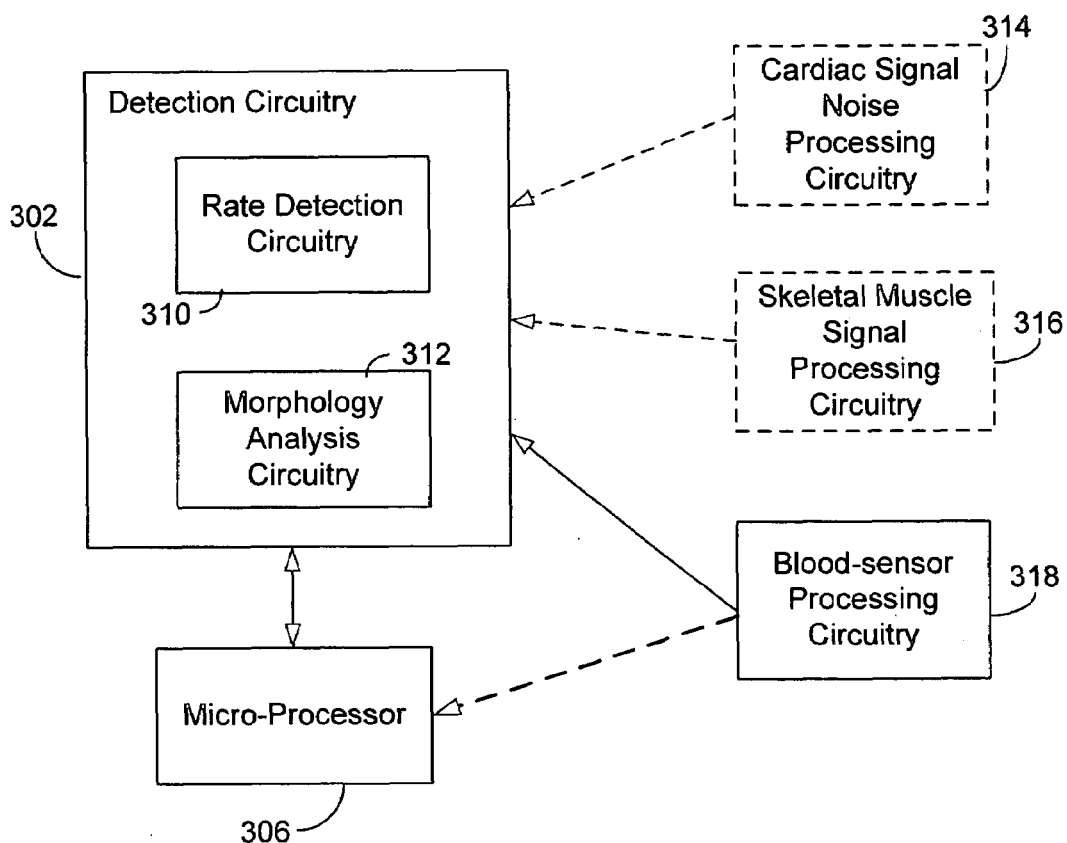
FIG. 1D is a block diagram illustrating various processing and detection components of a transthoracic cardiac sensing and/or stimulation device in accordance with an embodiment of the present invention.

FIG. 1D illustrates a configuration of detection circuitry 302, which is coupled to a micro-processor 306, of an ITCS device that includes one or both of rate detection circuitry 310 and morphological analysis circuitry 312 in combination with blood sensor processing circuitry 318. Detection and verification of arrhythmias may be accomplished using rate-based discrimination algorithms implemented by the rate detection circuitry 310 in combination with blood sensor processing circuitry 318. Arrhythmic episodes may also be detected and verified by morphology-based analysis implemented by the morphology analysis circuitry 312 in combination with blood sensor processing circuitry 318. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approaches disclosed in U.S. Pat. Nos. 6,487,443; 6,259,947; 6,141,581; 5,855,593; and 5,545,186, which are hereby incorporated herein by reference in their respective entireties.

An ITCS device may be implemented to include a subcutaneous electrode system that provides for cardiac sensing and arrhythmia therapy. According to this approach, an ITCS device may be implemented as a chronically implantable system that performs monitoring, diagnostic and/or therapeutic functions. The ITCS device may automatically detect and treat cardiac arrhythmias. In one configuration, the ITCS device includes a pulse generator and one or more electrodes that are implanted subcutaneously in the chest region of the body, such as in the anterior thoracic region of the body. The ITCS device may be used to provide atrial and ventricular therapy for bradycardia and tachycardia arrhythmias. Tachyarrhythmia therapy may include cardioversion, defibrillation and anti-tachycardia pacing (ATP), for example, to treat atrial or ventricular tachycardia or fibrillation. Bradycardia therapy may include temporary post-shock pacing for bradycardia or asystole. Methods and systems for implementing post-shock pacing for bradycardia or asystole are described in commonly owned U.S. Patent Application entitled "Subcutaneous Cardiac Stimulator Employing Post-Shock Transthoracic Asystole Prevention Pacing, Ser. No. 10/377,274, filed on Feb. 28, 2003, which is incorporated herein by reference in its entirety.

An ITCS device of a type described herein may be used within the structure of an advanced patient management (APM) system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies such as cardiac signal noise processing circuitry 314 and skeletal muscle signal processing circuitry 316 that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 1E:
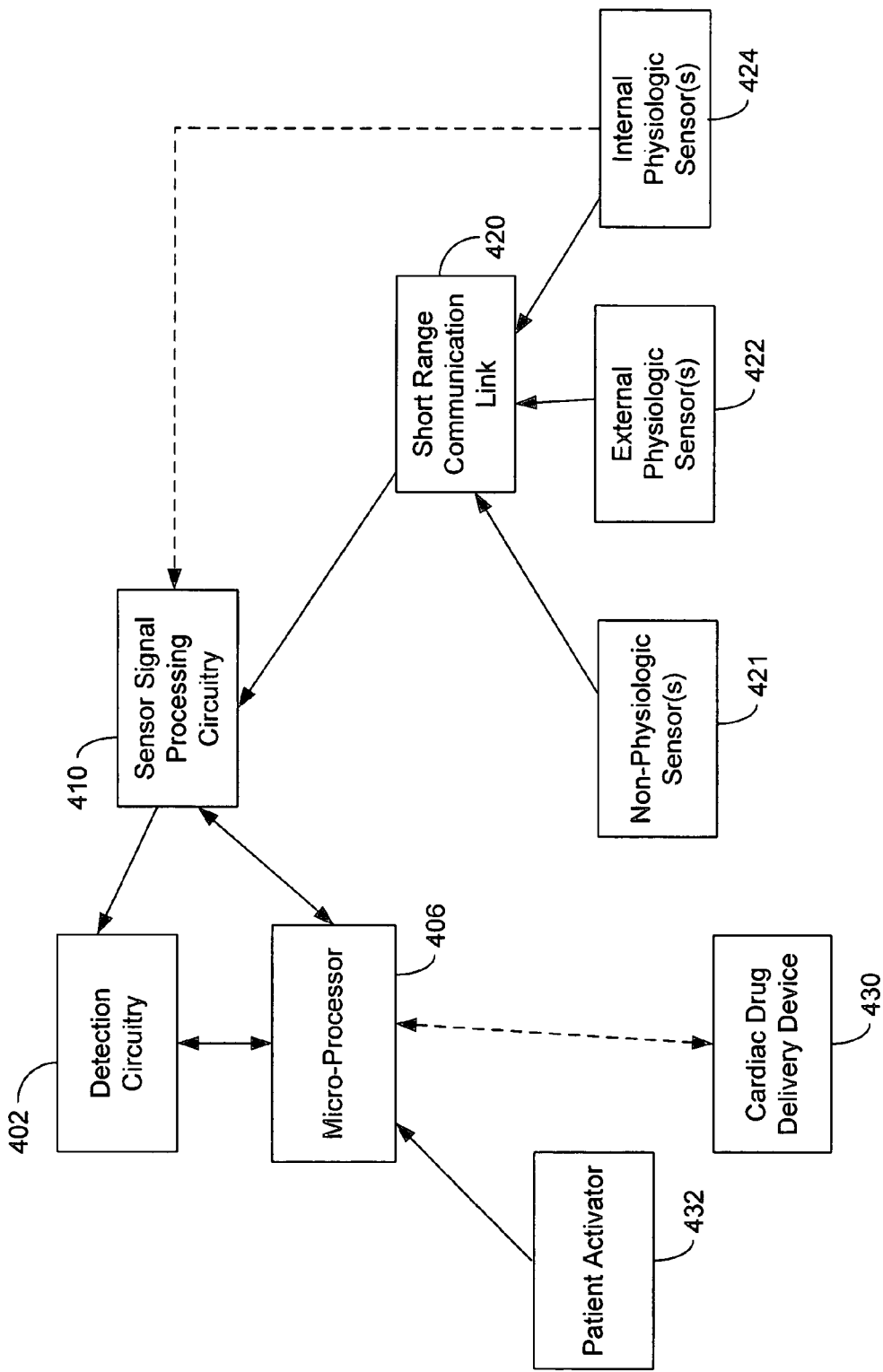
FIG. 1E is a block diagram illustrating one configuration of various ITCS device components in accordance with an embodiment of the present invention.

Turning now to FIG. 1E, there is illustrated a block diagram of various components of an ITCS device in accordance with one configuration. FIG. 1E illustrates a number of components that are associated with detection of various physiologic and non-physiologic parameters. As shown, the ITCS device includes a micro-processor 406, which is typically incorporated in a control system for the ITCS device, coupled to detection circuitry 402, patient activator 432, and optionally, cardiac drug delivery device 430. Sensor signal processing circuitry 410 can receive sensor data from a number of different sensors.

For example, an ITCS device may cooperate with, or otherwise incorporate, various types of non-physiologic sensors 421, external/cutaneous physiologic sensors 422, and/or internal physiologic sensors 424. Such sensors may include an acoustic sensor, an impedance sensor, an oxygen saturation sensor, a blood volume sensor, and a blood pressure sensor, for example. Each of these sensors 421, 422, 424 may be communicatively coupled to the sensor signal processing circuitry 410 via a short range wireless communication link 420. Certain sensors, such as an internal physiologic sensor 424, may alternatively be communicatively coupled to the sensor signal processing circuitry 410 via a wired connection (e.g., electrical or optical connection). A useful photoplethysmography sensor and techniques for using same that may be implemented in an ITCS device of the present invention are disclosed in U.S. Pat. No. 6,491,639, which is hereby incorporated herein by reference.

The components, functionality, and structural configurations depicted in FIGS. 1A-1E are intended to provide an understanding of various features and combination of features that may be incorporated in an ITCS device. It is understood that a wide variety of ITCS and other implantable cardiac monitoring and/or stimulation device configurations are contemplated, ranging from relatively sophisticated to relatively simple designs. As such, particular ITCS or cardiac monitoring and/or stimulation device configurations may include particular features as described herein, while other such device configurations may exclude particular features described herein.

Electrocardiogram signals often contain noise signals and artifacts that mimic true cardiac signals and various arrhythmias. Using a blood sensor in accordance with the present invention provides the ability to discriminate true arrhythmia conditions from various noisy conditions. Moreover, using a blood sensor in accordance with the present invention provides the ability to confirm that the signals upon which arrhythmia detection and therapy delivery decisions are made contain a cardiac signal (e.g., a QRS complex), rather than a spurious signal that may have features similar to those of a true cardiac signal. An ITCS device may be implemented to include multi-parameter cardiac signal verification and/or arrhythmia discrimination capabilities to improve noise rejection of cardiac ECG signals sensed by subcutaneous electrodes. This noise rejection/reduction approach advantageously reduces the risk of false positives for detection algorithms by providing multi-parameter arrhythmia discrimination.

For example, a non-electrophysiologic signal may be used to verify that the ECG signal contains a cardiac signal having a QRS complex, and that only ECG signals with QRS complexes are considered verified ECG signals. Subsequent cardiac rhythm analyses, including, in particular, arrhythmia analyses, may require that only verified ECG signals are used for computations of, for example, heart rate used for such analyses. This cardiac signal confirmation technique provides for more robust algorithms that are less susceptible to contamination from electrical interference and noise, thereby reducing incidences of inappropriate tachyarrhythmia therapy delivery.

One approach to cardiac signal confirmation involves determining temporal relationships between electrocardiogram signals and non-electrophysiologic signals. A detection window may, for example, be initiated in response to detecting an electrocardiogram signal, and used to determine whether a non-electrophysiologic signal is or is not received at a time falling within the detection window. For example, one arrhythmia detection approach uses the ECG signal to define a detection window. A non-electrophysiological source signal, such as a blood sensor signal, is then evaluated within the detection window for cardiac information. If the non-electrophysiological source signal includes a cardiac event within the window, then the ECG signal is corroborated as corresponding to a cardiac event. This may be used, for example, in a rate-based arrhythmia detection algorithm to provide a more robust rate than the rate calculated if only ECG information is used. The algorithm may, for example, only count ECG identified heart beats if the heart beats are corroborated by an associated non-electrophysiologically sensed heart beat.

Heart rates, for example, may be computed based on both a succession of electrocardiogram signals and a succession of non-electrophysiologic signals. These rates may be used to discriminate between normal sinus rhythm and the arrhythmia. The rates may be compared with arrhythmia thresholds, and used to determine absence of an arrhythmia, such as in response to a first rate exceeding a first arrhythmia threshold and a second rate failing to exceed a second arrhythmia threshold. The presence of an -arrhythmia may be determined using a morphology of the electrocardiogram signals, and then verified using the non-electrophysiologic signals.

In another embodiment of the present invention, defibrillation therapy delivery may be inhibited or withheld in response to detecting an arrhythmia using the electrocardiogram signals but failing to detect the arrhythmia using the non-electrophysiologic signal, such as a blood sensor signal. A method of sensing an arrhythmia and inhibiting therapy may involve sensing an electrocardiogram signal at a subcutaneous non-intrathoracic location. A detection window may be defined with a start time determined from the electrocardiogram signal. A signal associated with a non-electrophysiological cardiac source may be received and evaluated within the detection window. The presence or non-presence of a cardiac arrhythmia may be determined using the electrocardiogram signal, and confirmed by the presence of the cardiac arrhythmia as detected by the non-electrophysiological cardiac signal. The start time of a detection window used for confirmation may be associated with an inflection point of the electrocardiogram signal, such as a maxima or a minima. A correlation may be performed between the electrocardiogram signal and the non-electrophysiological cardiac signal.

Details of useful cardiac signal confirmation/verification techniques involving non-electrophysiologic signals are disclosed in commonly owned, co-pending U.S. patent application Ser. Nos. 10/804,471, filed Mar. 19, 2004, entitled "Multi-Parameter Arrhythmia Discrimination"; 10/784,478, filed Feb. 23, 2004, entitled "Subcutaneous Cardiac Signal Discrimination Employing Non-Electrophysiologic Signal"; and U.S. Patent Application entitled "Subcutaneous Cardiac Stimulation System with Patient Activity Sensing," filed Apr. 1, 2004 under Ser. No. 10/816,464, which are hereby incorporated herein by reference.

According to one embodiment, photoplethysmography is used to aid in noise discrimination when detecting various heart rhythms in the presence of electrical noise or artifacts. Because the additional discriminating signal is based on blood oxygen level or pulsatile blood volume level, and not based on electrical cardiac signals, this signal may provide information about a patient's rhythm state or hemodynamics even in the presence of electrical noise.

A subcutaneous sensor may be used to detect blood oximetry. One such sensor is a pulse oximetry sensor, for example. The blood oxygen level information may be used together with rate, curvature, and other ECG information to discriminate normal sinus with electrical noise from potentially lethal arrhythmias such as ventricular tachycardia and ventricular fibrillation. An ITCS device may utilize the characteristics of blood oxygen information combined with typical ECG information for discrimination.

In accordance with an embodiment of the present invention, subcutaneous photoplethysmography may be employed to develop a non-electrophysiological cardiac signal for detection and/or confirmation of cardiac rhythm. This feature employs a subcutaneous photoplethysmogram as part of a subcutaneous ICD system (e.g., ITCS device) as an alternative or additional signal to the electrocardiogram for detecting cardiac rhythm or hemodynamic state, particularly in the presence of electrical noise.

Photoplethysmography may be used subcutaneously for confirming patient cardiac arrhythmia detected by an implantable cardiovertor/defibrillator. Subcutaneous photoplethysmography may also be used to characterize patient hemodynamics for an implantable cardiovertor/defibrillator. For example, subcutaneous photoplethysmography may be used to evaluate afterload. Afterload is the systolic load on the left ventricle after it has started to contract. The resistance associated with afterload results from resistive forces of the vasculature that are overcome in order to push a bolus of blood into this vasculature during every heart beat. Hypertension or aortic stenosis could cause chronically increased afterload and lead to left ventricular hypertrophy and, subsequently, to heart failure.

Photoplethysmography may further be used subcutaneously for pulse oximetry to measure characteristics related to changes in patient oxygen saturation for an implantable cardiovertor/defibrillator. In general, it is desirable to reduce overall photoplethysmography energy, such as by utilizing it only for arrhythmia confirmation after other detection algorithms have been employed.

In one particular approach, a subcutaneous photoplethysmogram is used to confirm or verify that the cardiac signal used for cardiac rhythm analysis is indeed a cardiac signal, rather than a spurious signal, such as a skeletal noise signal. For example, the subcutaneous photoplethysmogram may be used to verify that the cardiac signal used to make tachyarrythmia therapy delivery decisions is an electrocardiogram indicative of the patient's actual heart rhythm. According to this approach, the subcutaneous photoplethysmogram is used primarily for verifying that the signal used for arrhythmia analysis and therapy delivery decisions is indeed the cardiac signal, which is distinct from using this signal to separately verify the presence or absence of an arrhythmia. It is understood, however, that the subcutaneous photoplethysmogram may be used as a signal to separately verify the presence or absence of an arrhythmia, exclusively or in addition to using this signal for cardiac signal confirmation.

For example, the control system processor may inhibit delivery of a tachyarrhythmia therapy until the ECG signal used to detect presence of the arrhythmia is confirmed to include a cardiac signal (e.g., QRS complex) using a photoplethysmic signal. The processor, for example, may inhibit delivery of the tachyarrhythmia therapy for a predetermined time period during which the verification processes is carried out, and withhold delivery of the tachyarrhythmia therapy upon expiration of the predetermined time period if such verification processes is unsuccessful or in response to cessation of the arrhythmia. The processor may deliver the tachyarrhythmia therapy in response to a successful outcome of the verification process. Also, the processor may immediately deliver the tachyarrhythmia therapy irrespective of the verification process in response to detection of a life-threatening arrhythmia.

Several benefits may be achieved through use of subcutaneous photoplethysmography. For example, subcutaneous photoplethysmography may be used to reduce the number of inappropriate shocks by improving shock specificity. It may also be used to provide for confirmation of ventricular arrhythmias based on the level of blood perfusion or relative change in blood perfusion. Further, subcutaneous photoplethysmography may be used to complement cardiac electrocardiogram-based algorithms by using a non-electric photo-based detection method. Subcutaneous photoplethysmography may also be used for redetection and reconfirmation of arrhythmias.

Figure 2:
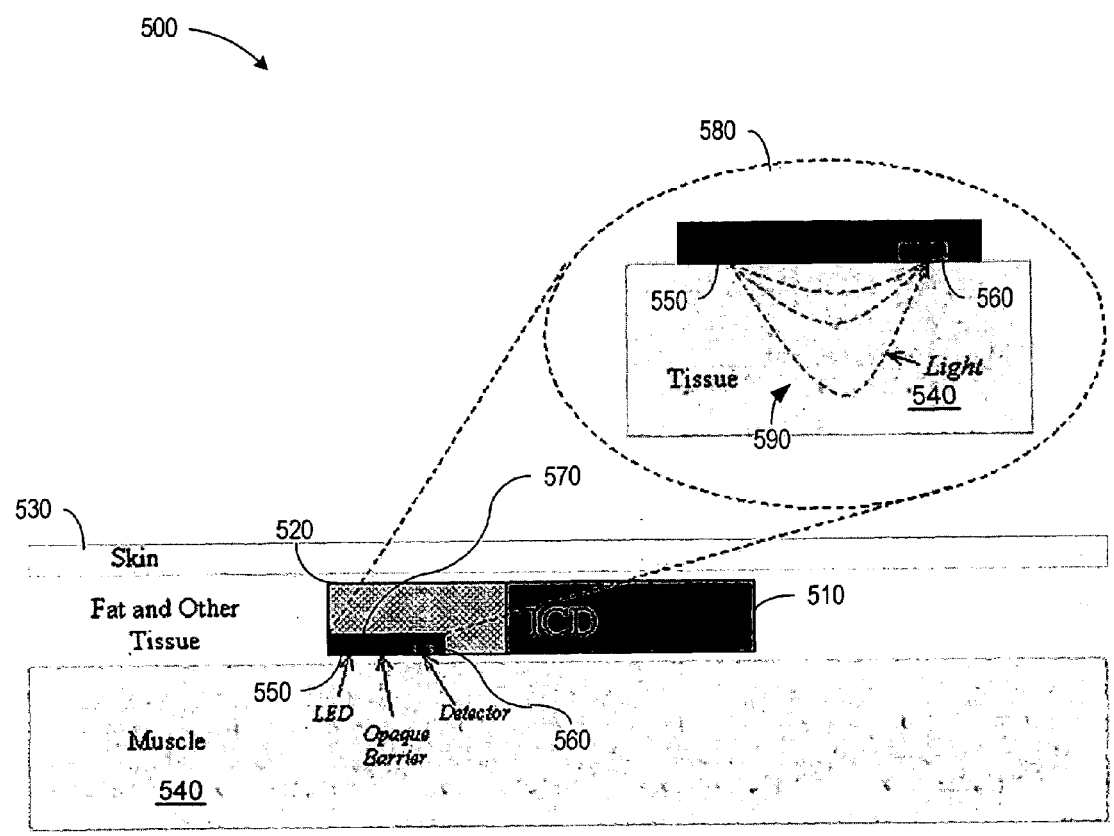
FIG. 2 is a plan view of a subcutaneously implanted ICD with photoplethysmography capability in accordance with an embodiment of the present invention.

FIGS. 2 through 7 illustrate various embodiments and processes associated with the use of subcutaneous blood sensing employed for detection and/or confirmation of a cardiac rhythm. FIG. 2 illustrates one implementation of a photoplethysmographic sensing system 500 suitable for use in a subcutaneous cardiac stimulator 510 (e.g., an ITCS device). FIG. 2 illustrates deployment of a subcutaneous photoplethysmographic sensor 520 in an orientation between a layer of skin 530 and a layer of muscle tissue 540. The illustrative example of FIG. 2 depicts a light source 550 (i.e., LED) and a detector 560 facing towards the muscle tissue 540. This orientation advantageously reduces interference from ambient light sources, thus reducing noise artifacts on the plethysmogram, particularly if an opaque barrier 570 is used to direct light into the detector 560. Other configurations may have the light source 550 and the detector 560 on the side or facing towards the skin.

When the cardiac stimulator 510 encounters an electrocardiogram that it cannot interpret, or to confirm detection of a hemodynamically unstable arrhythmia, the light source 550 is activated and the output of the photodetector 560 is synchronously measured. Algorithms in the cardiac stimulator 510 are then invoked to determine the pulse rate from the photoplethysmogram and inform therapy decisions. Measurements from this signal may also be used to inform or adapt electrocardiogram noise discrimination and/or arrhythmia detection algorithms.

Use of subcutaneous photoplethysmography in accordance with this embodiment advantageously provides for detection of cardiac rhythm in the presence of electrical noise or artifacts. The algorithm is robust, in that the photoplethysmogram is an optical signal and therefore not susceptible to the same noise sources as the ECG.

An expanded view 580 illustrates a light path 590 from the light source 550 to the detector 560. The perfusion of blood in the muscle tissue 540 affects the character of the light as it is reflected from the tissue 540 to the detector 560 along the path 590, providing blood information such as blood oxygen saturation level, blood volume, pulse, and other blood characteristics.

Figure 3:
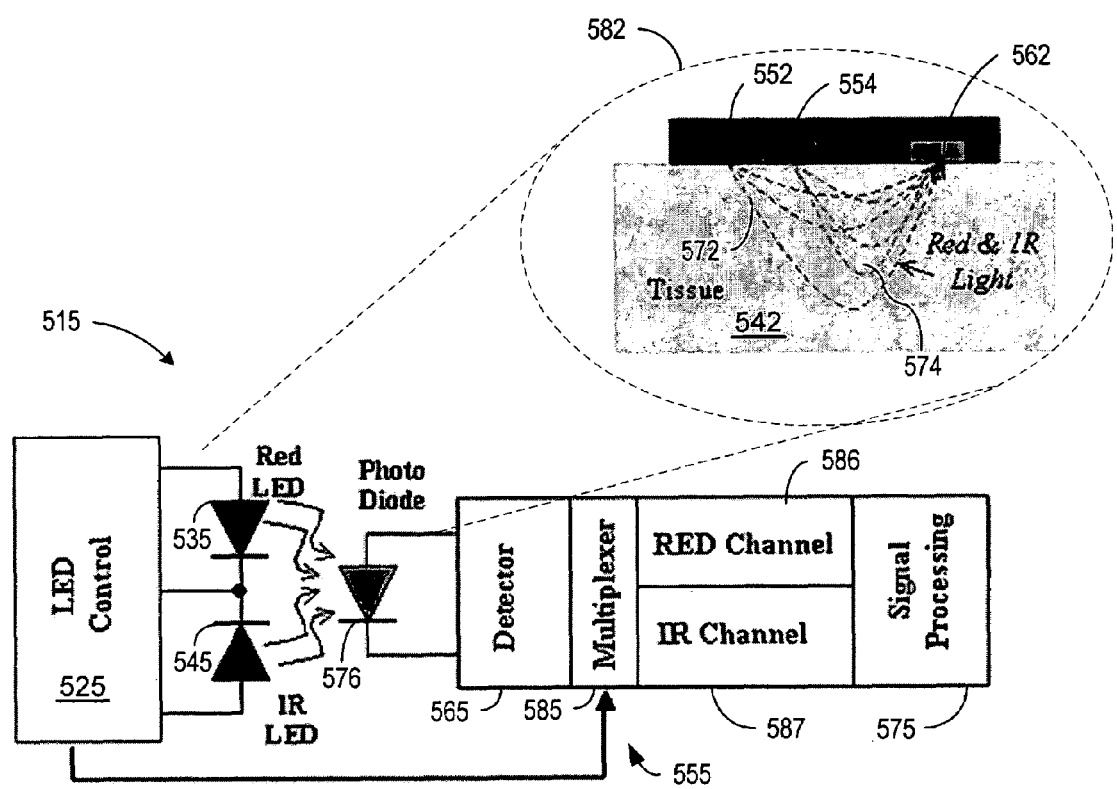
FIG. 3 is a block diagram illustrating a two-color photoplethysmographic system in accordance with an embodiment of the present invention.

The implementation shown in FIG. 3 includes an optical source circuit 515 that includes an LED control 525 respectively coupled to a Red LED 535 and an Infrared (IR) LED 545. Changes in oxygen saturation levels in the tissue 542 may be measured using two light sources and one detector. Typically, one light source has absorption characteristics that are generally unaffected by blood color change (such as the IR LED 545, emitting at ~960 nm), while the other light source has absorption characteristics that are sensitive to color change in the blood (such as the Red LED 535, emitting at ~660 nm). Due to potential errors in calculating absolute oxygen saturation using reflectance in areas of low perfusion, the embodiments illustrated in FIGS. 3 through 6 only monitor changes in oxygen saturation, and not absolute levels. The information from changes in oxygen saturation of the blood is sufficient to discriminate between potentially lethal arrhythmias and noise artifacts that could otherwise lead to unnecessary shocking of the patient without the discrimination.

Still referring to FIG. 3, an optical detection circuit 555 includes a detector 565 coupled to a photo diode 576. Processing circuitry 575 is coupled to the optical source circuit 515 and the optical detection circuit 555 in this configuration. The processing circuitry 575 includes a multiplexer 585 coupled to the LED control 525 and the detection circuit 555. A Red signal channel 586 and IR signal channel 587 are respectively coupled between the multiplexer 585 and the signal processing circuitry 675. The signal processing circuitry 575 operates on signals received from the Red signal channel 586 and the IR signal channel 587, and employs various algorithms to evaluate such signals for cardiac rhythm detection and/or confirmation, including arrhythmia detection and confirmation.

A magnified view 582 illustrates a light path 572 from a first light source 552 and a light path 574 from a second light source 554 to a detector 562. The perfusion of blood in the muscle tissue 542 affects the character of the light as it is reflected from the tissue 542 to the detector 562 along paths 572 and 574, providing blood information such as blood oxygen saturation level, blood volume, pulse, or other blood characteristics.

Figure 4:
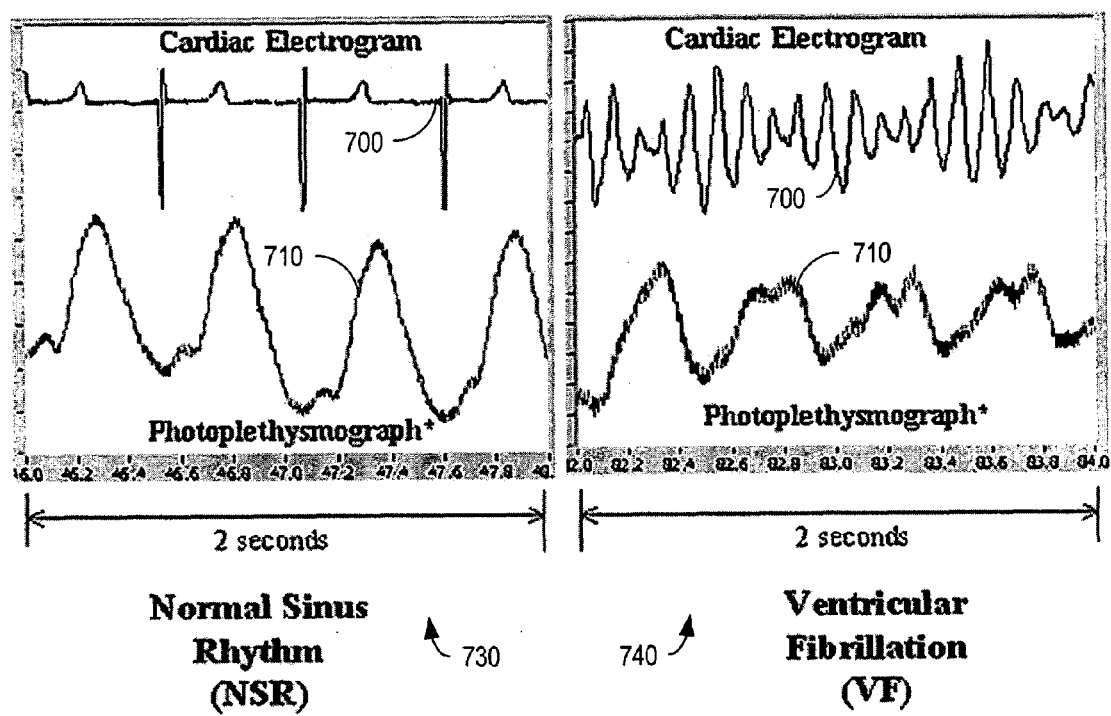
FIG. 4 is a graph illustrating signals from normal sinus rhythm versus ventricular fibrillation.
Figure 5:
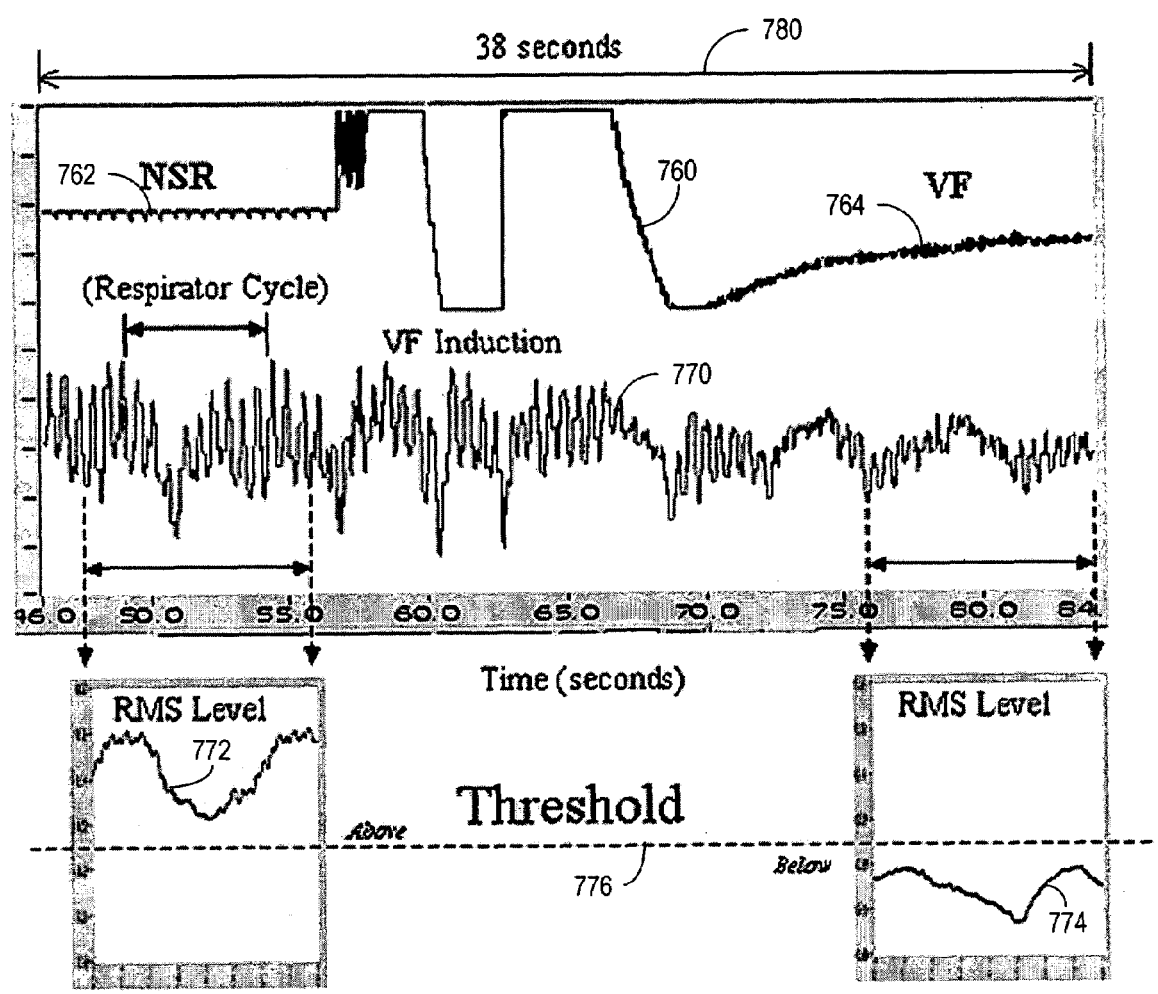
FIG. 5 is a graph illustrating RMS photoplethysmogram levels during normal sinus rhythm versus ventricular fibrillation.

FIGS. 4 and 5 are graphs of data taken from a live porcine subject, and illustrate an example of combining electrocardiography and photoplethysmography to differentiate normal sinus rhythm from arrhythmia in accordance with an embodiment of the present invention. FIG. 4 illustrates a cardiac electrocardiogram 700 and a photoplethysmogram 710 presented over a 2 second duration for a normal sinus rhythm condition 730 and a ventricular fibrillation condition 740. FIG. 5 illustrates a cardiac electrocardiogram 760 and a time correlated photoplethysmogram 770 during a 38 second period 780 in which a normal sinus rhythm 762 is followed by a ventricular fibrillation event 764. FIGS. 4 and 5 demonstrate that both the cardiac electrocardiograms 700, 760 and photoplethysmograms 710, 770 change significantly in character when the normal sinus rhythm 730, 762 devolves into the ventricular fibrillation 740, 764 conditions.

Referring back to FIG. 4, note that the scale of the normal sinus rhythm 730 graph and the ventricular fibrillation 740 graph are different. Although the photoplethysmogram 710 of the ventricular fibrillation 740 looks comparable to the photoplethysmogram 710 of the normal sinus rhythm 730, the peak-to-peak amplitude of the photoplethysmogram 710 in the ventricular fibrillation 740 graph is significantly smaller than the peak-to-peak amplitude of the photoplethysmogram 710 in the normal sinus rhythm 730 graph. The ordinate scale of the ventricular fibrillation 740 graph is equal to the ordinate scale of the normal sinus rhythm 730 graph.

Referring now to FIG. 5, a RMS blood oxygen level 772 corresponds to the normal sinus rhythm 762, and a RMS blood oxygen level 774 corresponds to the ventricular fibrillation event 764. A threshold 776 may be predetermined or adaptively adjusted to help differentiate between the normal sinus rhythm 762 and the ventricular fibrillation event 764. The time period between the normal sinus rhythm 762 and the ventricular fibrillation event 764 indicates a loss of data in the electrocardiogram 760 during the intentional induction of the ventricular fibrillation 764.

Figure 6A:
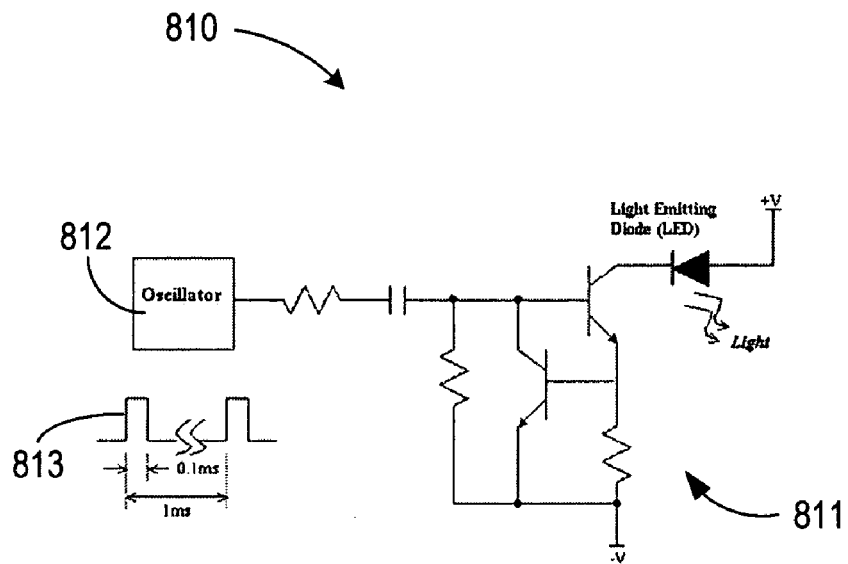
FIGS. 6A and 6B are circuit diagrams of an LED transmission circuit and an LED detection circuit in accordance with an embodiment of the present invention.

FIG. 6A is a schematic of an LED current source section 810 of a photoplethysmography circuit in accordance with an embodiment of the present invention. As is illustrated in FIG. 6A, the current source section 810 is configured as a constant current source, using a source LED circuit 811, and is driven by an oscillator 812 that may produce drive pulses 813 having a period of 1 ms and a pulse width of 0.1 ms, for example.

Figure 6B:
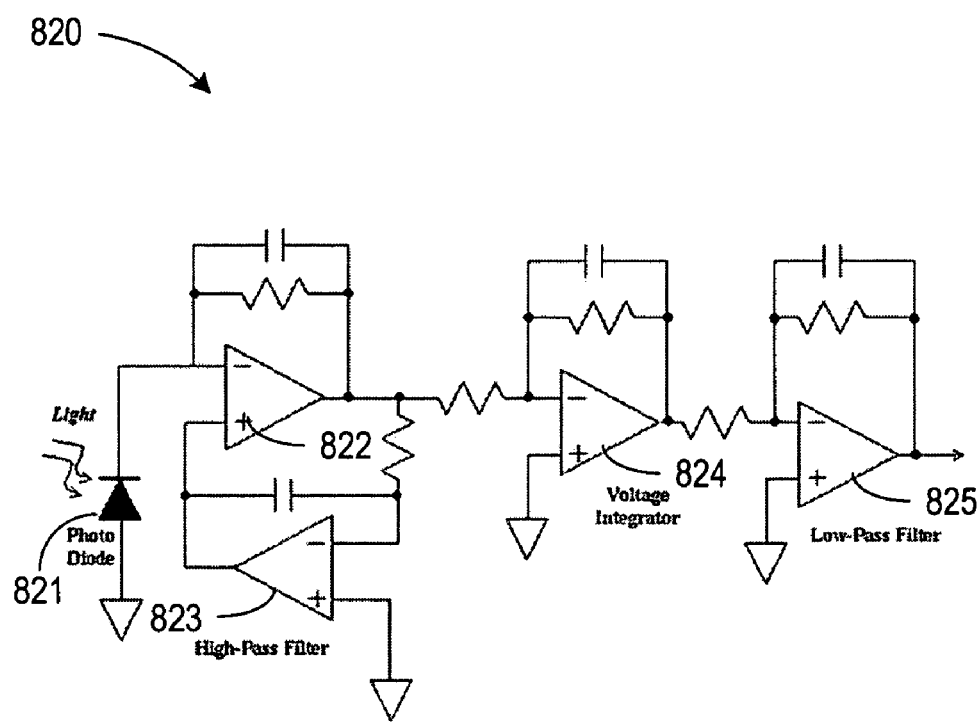

FIG. 6B is a schematic of a photo detector section 820 of a photoplethysmography circuit in accordance with an embodiment of the present invention. The detector section shown in FIG. 6B includes a photo diode 821, a light current to voltage amplifier 822, a high pass filter 823, a voltage integrator 824, and a low pass filter 825. The circuits illustrated in FIGS. 6A and 6B are useful for providing a photoplethysmic signal, such as signal 770 shown in FIG. 5.

Figure 7:
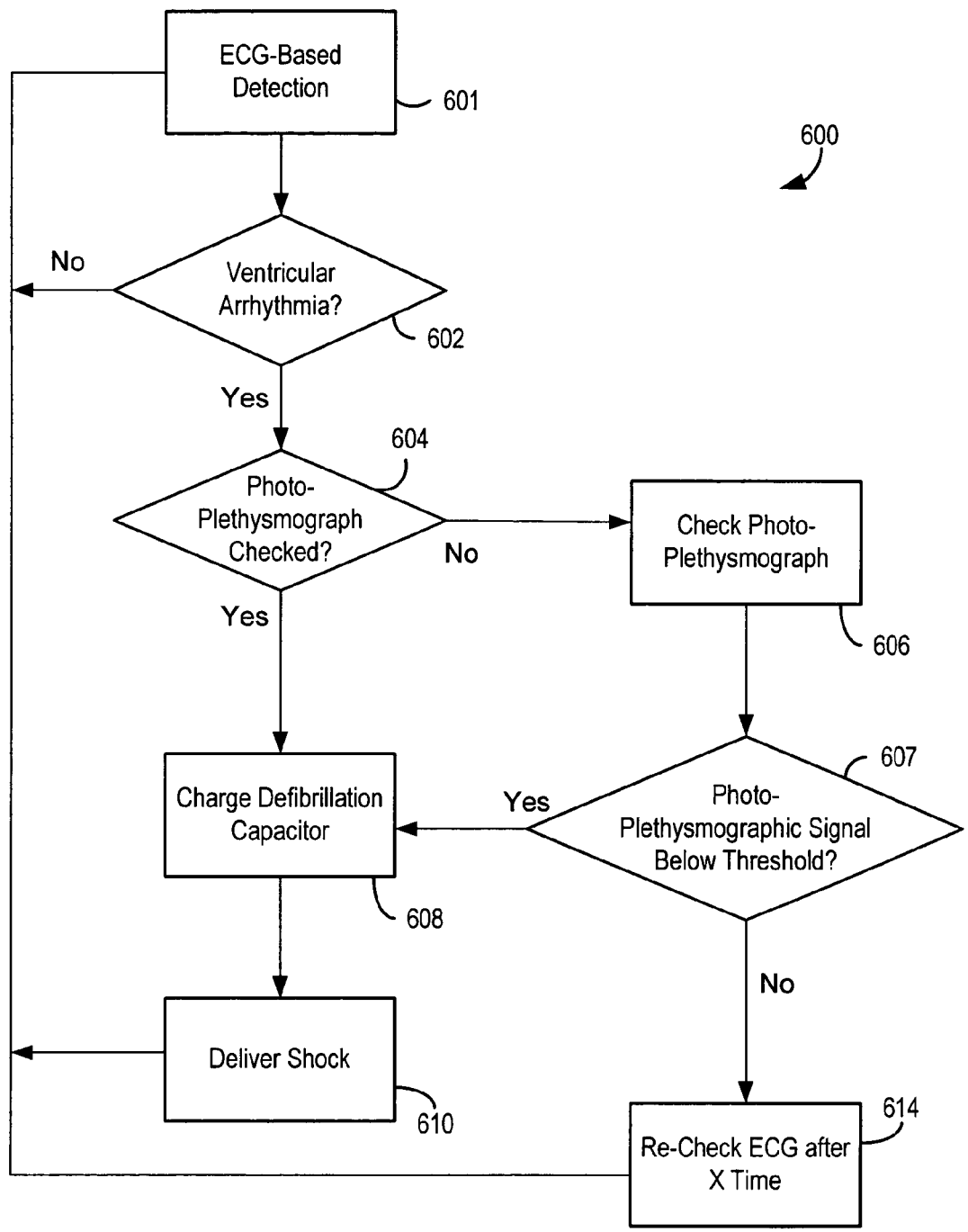
FIG. 7 is a flow chart of a method of arrhythmia discrimination in accordance with an embodiment of the present invention.

FIG. 7 illustrates various processes associated with one method of utilizing subcutaneous photoplethysmography in combination with electrocardiogram-based rhythm detection. The method illustrated in FIG. 7 presents details concerning energy utilization. The photoplethysmography circuitry may be enabled only after other arrhythmia detection methods have been employed, such as cardiac electrocardiogram-based algorithms. Photoplethysmography may be used only before potentially delivering the shock, to conserve energy. The circuitry may be disabled when use of the photoplethysmogram is completed. According to one implementation, if photoplethysmography is used for 10 seconds, the additional energy required is about 0.5 joules. This energy is very low when compared with the energy used for defibrillation (>5 joules). Therefore, discriminating one electrocardiogram identified arrhythmia event as noise using photoplethysmography has the potential to save over 4.5 joules. It is understood that eliminating unnecessary shocks extends the useful life of the ITCS, while simultaneously improving patient comfort.

With reference to FIG. 7, and with further reference to FIGS. 4 and 5, an ECG-based detection algorithm 600 is employed to detect cardiac arrhythmias. If a ventricular arrhythmia is detected 602 using ECG based detection 601, a determination 604 is performed to see if the photoplethysmogram has been checked. A check 606 of an acquired photoplethysmogram is performed. If the photoplethysmogram indicates or confirms the presence of a ventricular arrhythmia, such as by using a threshold 607, the defibrillation capacitor is charged 608 and a shock is delivered 610. It is noted that a ventricular arrhythmia re-verification routine may be performed during capacitor charging prior to shock delivery.

If the photoplethysmogram signal exceeds the predetermined threshold 607, such as the threshold shown in FIG. 5 (note that an RMS level of the photoplethysmogram may be used in this comparison), a recheck 614 of the ECG signal is made after a predetermined time period.

In the methodology depicted in FIG. 7, the photoplethysmic sensor that produces the photoplethysmogram signal may be selectively powered-up and powered-down. For example, the photoplethysmic sensor may be in a powered-down state until a tachyarrhythmia is detected using the ECG signal, such as at blocks 601 and 602 in FIG. 7. The photoplethysmic sensor may remain powered-on until completion of the cardiac signal and/or arrhythmia detection verification processes. For example, the photoplethysmic sensor may be powered-down after completing the processes associated with blocks 606 and 607, and prior to charging the defibrillation capacitor at block 608, which may take as long as about 20 seconds to fully charge the capacitor(s).

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable subcutaneous device, comprising:
a housing configured for subcutaneous non-intrathoracic placement;
detection circuitry provided in the housing and configured to produce a cardiac electrophysiologic signal;
energy delivery circuitry provided in the housing;
at least one electrode configured for subcutaneous non-intrathoracic placement and coupled to the detection and energy delivery circuitry;
an implantable blood sensor configured to produce a blood sensor signal; and
a processor provided in the housing and coupled to the blood sensor and the detection and energy delivery circuitry, the processor configured to use the blood sensor signal to verify that the cardiac electrophysiologic signal comprises a cardiac signal, and configured to evaluate a cardiac rhythm using the blood sensor signal and the cardiac electrophysiologic signal comprising the cardiac signal.

2. The device of claim 1, wherein the blood sensor is configured for subcutaneous non-intrathoracic placement.

3. The device of claim 1, wherein the blood sensor is provided in or on the housing.

4. The device of claim 1, wherein the blood sensor comprises a sensor configured for optical signal sensing.

5. The device of claim 1, wherein the blood sensor comprises a blood oxygen saturation sensor.

6. The device of claim 1, wherein the blood sensor comprises a pulse oximeter.

7. The device of claim 1, wherein the blood sensor comprises a pulse oximeter, the pulse oximeter comprising at least two light-emitting diodes and at least one photodetector.

8. The device of claim 7, wherein a photodetector detection threshold is periodically adjusted to account for signal variations.

9. The device of claim 1, wherein the blood sensor comprises a pulse oximeter, the pulse oximeter comprising a first light-emitting diode having a peak light-emission wavelength within a range of about 550 nm and about 750 nm, and a second light-emitting diode having a peak light-emission wavelength within a range of about 750 nm and about 1050 nm.

10. The device of claim 1, wherein the blood sensor includes photoplethysmography circuitry.

11. The device of claim 1, wherein the processor identifies the cardiac rhythm as a tachyarrhythmia using the cardiac electrophysiologic signal and the blood sensor signal.

12. The device of claim 1, wherein the processor identifies the cardiac rhythm as a tachyarrhythmia using the cardiac electrophysiologic signal and a relative change in the blood sensor signal.

13. The device of claim 1, wherein the processor selectively activates and deactivates the blood sensor.

14. The device of claim 1, wherein the processor, in response to detecting a tachyarrhythmia using the cardiac electrophysiologic signal, activates the blood sensor and evaluates the tachyarrhythmia using the cardiac electrophysiologic signal and the blood sensor signal.

15. The device of claim 14, wherein the processor confirms presence of the tachyarrhythmia using the cardiac electrophysiologic signal and the blood sensor signal.

16. The device of claim 15, wherein the processor, in response to confirming presence of the tachyarrhythmia, delivers a therapy that treats the tachyarrhythmia, the processor deactivating the blood sensor before or after delivery of the therapy.

17. The device of claim 15, wherein the processor inhibits delivery of a tachyarrhythmia therapy until the processor confirms presence of the tachyarrhythmia using the blood sensor signal.

18. The device of claim 1, wherein the processor determines a hemodynamic state using the cardiac electrophysiologic signal and the blood sensor signal.

19. The device of claim 1, wherein the processor, in response to detecting an unidentifiable cardiac rhythm using the cardiac electrophysiologic signal, activates the blood sensor facilitating identification of the unidentifiable cardiac rhythm using the blood sensor signal.

20. The device of claim 1, wherein the at least one electrode is coupled to the housing via a lead and wherein the housing further comprises at least one housing electrode.

21. The device of claim 1, wherein the processor uses the blood sensor signal for assessing cardiac function.

22. The device of claim 1, wherein the processor uses the blood sensor signal for assessing oxygen saturation.

23. The device of claim 1, wherein the processor uses the blood sensor signal for assessing afterload.

24. The device of claim 23, wherein the processor assesses afterload by analyzing the morphology of the blood sensor signal.

25. A rhythm evaluation method, comprising:
sensing an electrocardiogram signal at a subcutaneous non-intrathoracic location;
acquiring a blood sense signal from a subcutaneous non-intrathoracic sensing location;
verifying that, using the blood sense signal, the electrocardiogram signal comprises a cardiac signal; and
evaluating a cardiac rhythm using the blood sense signal and the electrocardiogram signal comprising the cardiac signal.

26. The method of claim 25, wherein evaluating the cardiac rhythm comprises detecting a tachyarrhythmia using one or both of the electrocardiogram signal and the blood sense signal.

27. The method of claim 26, wherein detecting the tachyarrhythmia comprises performing a rate based analysis of the electrocardiogram signal.

28. The method of claim 26, wherein detecting the tachyarrhythmia comprises performing a morphology based analysis of the electrocardiogram signal.

29. The method of claim 26, wherein detecting the tachyarrhythmia comprises analyzing an activation pattern of the electrocardiogram signal using a plurality of electrodes.

30. The method of claim 26, further comprising treating the tachyarrhythmia.

31. The method of claim 25, wherein evaluating the cardiac rhythm comprises confirming presence of a tachyarrhythmia using the electrocardiogram signal and the blood sense signal.

32. The method of claim 25, wherein evaluating the cardiac rhythm comprises detecting a tachyarrhythmia using the electrocardiogram signal, and confirming presence of the tachyarrhythmia using the blood sense signal.

33. The method of claim 25, wherein evaluating the cardiac rhythm comprises detecting a tachyarrhythmia using the electrocardiogram signal, and discerning the detected tachyarrhythmia from noise using the blood sense signal.

34. The method of claim 25, wherein evaluating the cardiac rhythm comprises detecting a cardiac arrhythmia by performing a correlation between the electrocardiogram signal and the blood sense signal.

35. The method of claim 25, wherein evaluating the cardiac rhythm comprises detecting a cardiac tachyarrhythmia, and the method further comprises inhibiting delivery of a tachyarrhythmia therapy until presence of the tachyarrhythmia is confirmed using the blood sense signal.

36. The method of claim 25, wherein acquiring the blood sense signal comprises selectively powering-up and powering-down a blood sensor that produces the blood sense signal.

37. The method of claim 25, wherein evaluating the cardiac rhythm comprises:
detecting a tachyarrhythmia using the electrocardiogram signal;
powering-up a blood sensor that produces the blood sense signal in response to detecting the tachyarrhythmia;
confirming presence of the tachyarrhythmia using the blood sense signal; and
powering-down the blood sensor after confirming presence of the tachyarrhythmia.

38. The method of claim 37, further comprising:
treating the tachyarrhythmia; and
powering-down the blood sensor before or after treating the tachyarrhythmia.

39. The method of claim 25, wherein the blood sense signal comprises blood perfusion information.

40. The method of claim 25, wherein the blood sense signal comprises blood oxygen saturation information.

41. The method of claim 25, wherein the blood sense signal comprises photoplethysmographic information.

42. The method of claim 25, wherein the blood sense signal comprises pulse oximetry information.

43. An implantable subcutaneous device, comprising:
means for sensing an electrocardiogram signal at a subcutaneous non-intrathoracic location;
means for acquiring a blood sense signal from a subcutaneous non-intrathoracic sensing location;
means for verifying that, using the blood sense signal, the electrocardiogram signal comprises a cardiac signal; and
means for evaluating a cardiac rhythm using the blood sense signal and the electrocardiogram signal comprising the cardiac signal.

44. The device of claim 43, wherein the evaluating means further comprises means for detecting a tachyarrhythmia using one or both of the electrocardiogram signal and the blood sense signal.

45. The device of claim 44, further comprising means for treating the tachyarrhythmia.

46. The device of claim 43, wherein the evaluating means further comprises means for detecting a tachyarrhythmia and means for confirming presence of the tachyarrhythmia.

47. The device of claim 43, wherein the evaluating means comprises means for detecting a tachyarrhythmia using the electrocardiogram signal, and means for confirming presence of the tachyarrhythmia using the blood sense signal.

48. The device of claim 43, wherein the acquiring means comprises means for selectively powering-up and powering-down the means for sensing an electrocardiogram signal.

49. The device of claim 43, wherein the evaluating means comprises means for assessing cardiac function.

50. The device of claim 43, wherein the evaluating means comprises means for assessing afterload.

51. The device of claim 43, wherein the evaluating means comprises means for assessing oxygen saturation.

52. The device of claim 43, wherein the evaluating means comprises means for assessing changes in oxygen saturation.

* * * * *